(12) United States Patent
Braddell et al.

(10) Patent No.: US 7,659,547 B2
(45) Date of Patent: Feb. 9, 2010

(54) LED ARRAY

(75) Inventors: Jules Braddell, Cork (IE); Kieran Kavanagh, County Cork (IE)

(73) Assignee: Phoseon Technology, Inc., Hillsboro, OR (US)

(*) Notice: Subject to any disclaimer, the term of this patent is extended or adjusted under 35 U.S.C. 154(b) by 0 days.

(21) Appl. No.: 10/991,499

(22) Filed: Nov. 19, 2004

(65) Prior Publication Data

US 2005/0087750 A1     Apr. 28, 2005

Related U.S. Application Data

(63) Continuation of application No. PCT/IE03/00082, filed on May 22, 2003.

(30) Foreign Application Priority Data

May 22, 2002   (IE) ................................ 2002/0398

(51) Int. Cl.
H01L 33/00 (2006.01)

(52) U.S. Cl. .............. 257/98; 257/79; 257/88; 257/92; 257/100; 257/E33.001

(58) Field of Classification Search .......... 257/79, 257/81, 88, 92, 93, 98, 100
See application file for complete search history.

(56) References Cited

U.S. PATENT DOCUMENTS

| | | | |
|---|---|---|---|
| 4,530,040 A | 7/1985 | Petterson | |
| 5,449,926 A * | 9/1995 | Holm et al. | 257/88 |
| 5,469,347 A * | 11/1995 | Duve et al. | 362/245 |
| 5,479,029 A | 12/1995 | Ikawa et al. | |
| 5,555,038 A | 9/1996 | Conway | |
| 6,155,699 A | 12/2000 | Miller et al. | |
| 6,222,207 B1 | 4/2001 | Carter-Coman et al. | |
| 6,258,618 B1 | 7/2001 | Lester | |
| 6,366,017 B1 | 4/2002 | Antoniadis et al. | |
| 6,424,399 B1 * | 7/2002 | Shimada et al. | 349/147 |
| 6,441,873 B2 * | 8/2002 | Young | 349/43 |
| 6,445,124 B1 * | 9/2002 | Asai et al. | 313/495 |
| 6,869,635 B2 * | 3/2005 | Kobayashi | 427/66 |
| 2002/0151941 A1 * | 10/2002 | Okawa et al. | 607/99 |

FOREIGN PATENT DOCUMENTS

| | | |
|---|---|---|
| EP | 0560605 | 9/1993 |
| JP | 59035492 | 2/1984 |
| JP | 2003268042 A | 9/2003 |
| WO | WO02086972 | 10/2002 |

* cited by examiner

*Primary Examiner*—Wai-Sing Louie
(74) *Attorney, Agent, or Firm*—Marger Johnson & McCollom, P.C.

(57) ABSTRACT

An illuminator (1) has bare semiconductor die light emitting diodes (7) on pads (11) of Ag/Ni/Ti material. A Si wafer (13) has a rough upper surface, and this roughness is carried through an oxide layer (12) and the pads (11) to provide a rough but reflective upper surface of the pads (11), thus forming a diffuser. Epoxy encapsulant (9) is deposited in a layer over the diodes (7) and the pads (11), and it is index matched with a top diffuser plate (8) of opal glass.

10 Claims, 3 Drawing Sheets

LED ARRAY

This is a continuation of PCT/IE03/00082 filed May 22, 2003 and published in English.

FIELD OF THE INVENTION

The invention relates to illuminators for applications such as machine vision.

PRIOR ART DISCUSSION

In general there is a requirement in many applications such as machine vision, photodynamic therapy and general illumination for an LED based illuminator in either continuous or strobe operation with some or all of the following properties:
 (a) A required level of uniformity.
 (b) A required illuminance in Lux or $mW/cm^2$
 (c) A required luminance in $cd/m^2$ or $W/m^2sr$
 (d) A required luminous flux or total radiated flux in Lumens or mW
 (e) Compact size to fit within constraints.
 (f) To be of sufficient optical-electrical conversion efficiency to reduce the power consumption of the illuminator and reduce the thermal load on individual light sources.
 (g) To minimise the thermal resistance from the light source to the outside environment hence reducing the operating junction temp of the light sources leading to an improved operating performance and reliability.

It is known to provide an array of "bare" semiconductor die mounted on a substrate to address these requirements, as described in U.S. Pat. No. 5,936,353. However, it appears that efficiency of light transmission at the required target area from the diodes could be improved.

SUMMARY OF THE INVENTION

According to the invention, there is provided an illuminator comprising a substrate, semiconductor diodes placed on the substrate, an electrical drive for the diodes, a layer of encapsulant over the diodes and the substrate, and a diffuser.

The combination of an encapsulant and a diffuser helps to achieve excellent robustness and optical efficiency, in turn leading to compactness.

In one embodiment, the substrate is the diffuser, the substrate being of a reflect material having a diffusing rough upper surface between the diodes.

In another embodiment, the substrate comprises a metal providing the diffusing rough surface.

In a further embodiment, the metal is Ag.

In one embodiment, the Ag is a layer over layers of Ni and Ti.

In another embodiment, the substrate comprises a Si layer having a rough upper surface, an $SiO_2$ oxide on the Si layer upper surface and having a rough upper surface, and at least one metal layer over the $SiO_2$ oxide layer and having a rough upper surface.

In a further embodiment, the substrate comprises conductive pads on which the diodes are placed.

In one embodiment, the ratio of the footprint of the diodes to that of the pads is equal to or less than approximately 1:50.

In another embodiment, the pads are of rectangular shape in plan.

In a further embodiment, there is a two-dimensional array of pads, and the diodes are connected in series along lines of the array between end rails.

In one embodiment, alternate lines of diodes are located at opposed ends of their pads.

In another embodiment, the diffuser comprises a top diffuser mounted on the encapsulant.

In a further embodiment, the encapsulant and the top diffuser are index matched.

In one embodiment, the top diffuser comprises an opal glass diffuser plate.

In another aspect, the invention provides a method of producing an illuminator comprising the steps of:
 providing a base layer of substrate material having a rough upper surface;
 applying a top layer of substrate reflective material over the base layer so that surface roughness of the base layer upper surface is carried through to the top layer upper surface;
 placing light emitting diodes in the form of bare semiconductor die on the substrate; and
 applying encapsulant over the diodes and the substrate.

This is a very simple and effective way of simultaneously providing both a suitable substrate and also a diffuser for an illuminator.

In one embodiment, the base layer comprises silicon.

In another embodiment, the base layer further comprises silicon dioxide.

In a further embodiment, the silicon is a wafer having a rough upper surface, and the silicon dioxide is grown on said rough upper surface.

In one embodiment, the top layer comprises Ag.

In another embodiment, the method comprises the further step of etching the top layer to define pads.

In a further embodiment, the pads have a size such that the ratio of footprint of the diodes to that of the pads is equal to or less than approximately 1:50.

DETAILED DESCRIPTION OF THE INVENTION

Brief Description of the Drawings

The invention will be more clearly understood from the following description of some embodiments thereof, given by way of example only with reference to the accompanying drawings in which:—

DESCRIPTION OF THE EMBODIMENTS

Figure 1:
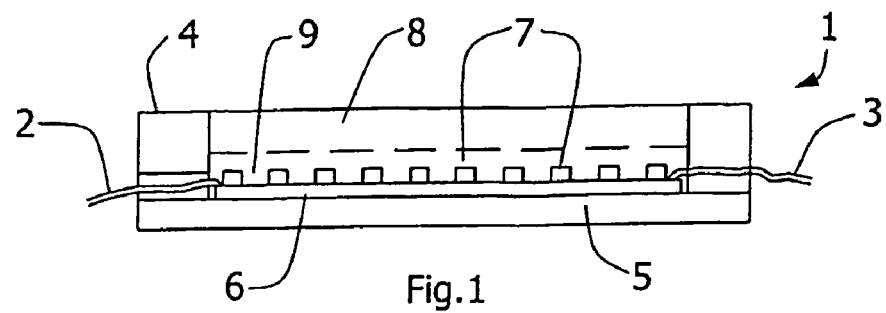
FIG. 1 is a diagrammatic cross-sectional side view of an illuminator of the invention.

Referring to FIG. 1 an illuminator 1 comprises electrical conductors 2 and 3 extending through an Al casing side wall 4 and over an Al casing base 5. The conductors 2 and 3 are connected to a substrate 6 on the casing base 5. Light emitting diodes 7 in the form of bare semiconductor die are mounted on the substrate 6. An opal glass diffuser plate 8 is mounted between the casing side walls 4 and over the diodes 7. The spacing between the diffuser 8 and the substrate 6 and the diodes 7 is filled with an epoxy encapsulant 9, the epoxy 9 being index matched to the diffuser 8.

Figure 2:
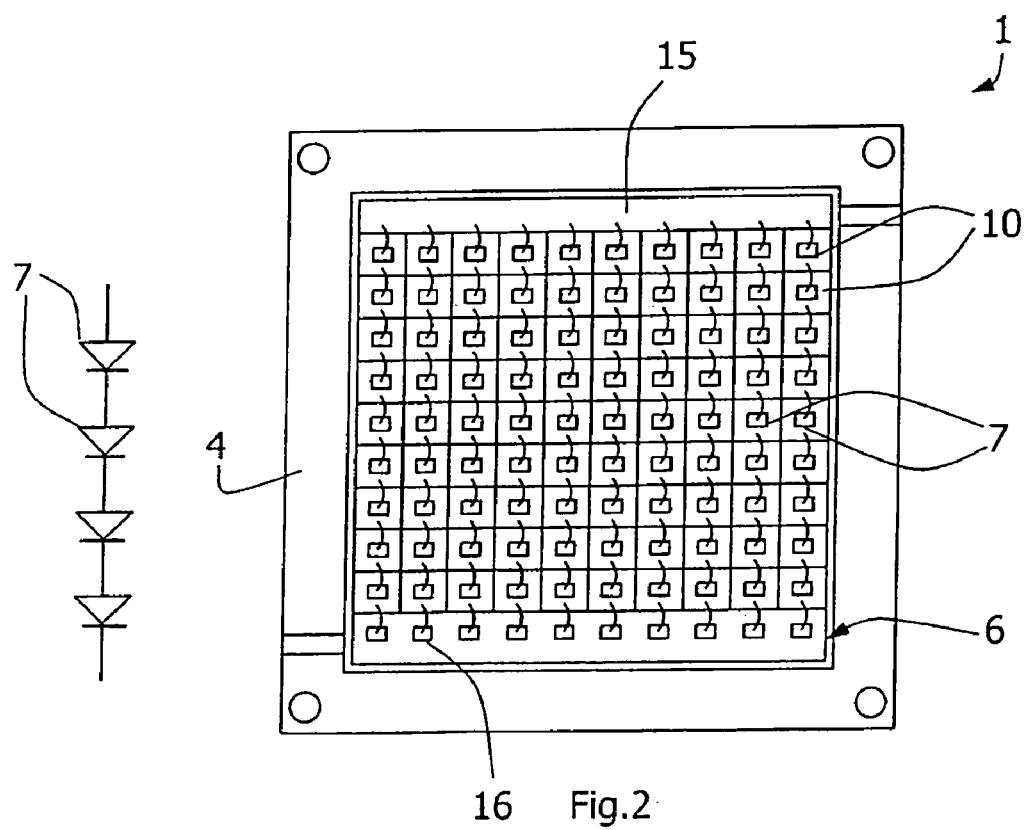
FIG. 2 is a diagrammatic plan view showing electrical connection of the diodes.

Referring to FIG. 2 the diodes 7 are shown diagrammatically to illustrate the electrical interconnection with wire bonds 10. The substrate 6 comprises metal pads 11 of rectangular shape, on each of which there is a diode 7. Each diode 7 is connected by a wire bond 10 to the next pad 11 in succession in columns between rails 15 and 16. The series interconnection of a column is also illustrated with an electrical schematic in FIG. 2.

Figure 3:
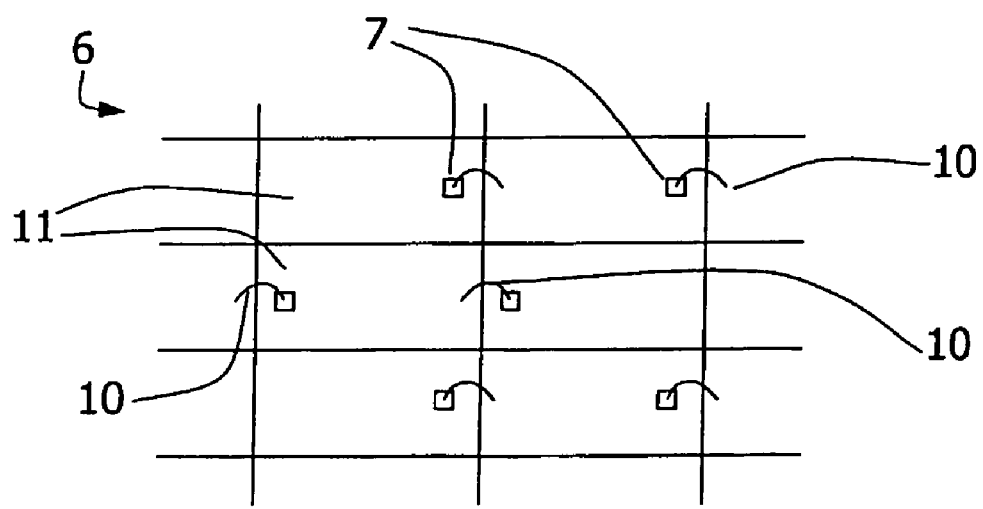
FIG. 3 is a more detailed plan view showing the arrangement of the diodes on the substrate.

Referring to FIG. 3 the physical arrangement of the diodes 7 is shown. Each pad 11 is of size 4 mm×3 mm and each diode 7 is 0.5 mm×0.5 mm. In other embodiments the diodes 7 may be smaller, for example 0.25 mm×0.25 mm. Thus, the ratio of footprint size of each diode 7 to the pad 11 is c. 1:50 or less. This is in contrast to current teaching in this art towards ever higher density of diodes within the confines imposed by heat dissipation requirements.

It also be appreciated from FIG. 3 that the diodes 7 are not centrally mounted on the pads 11. Instead they are on opposed ends of the pads 11 in alternate columns to achieve a more uniform distribution and a large wire bond connection area. Even better uniformity may be activated if they are arranged in a hexagonal pattern.

Figure 4:
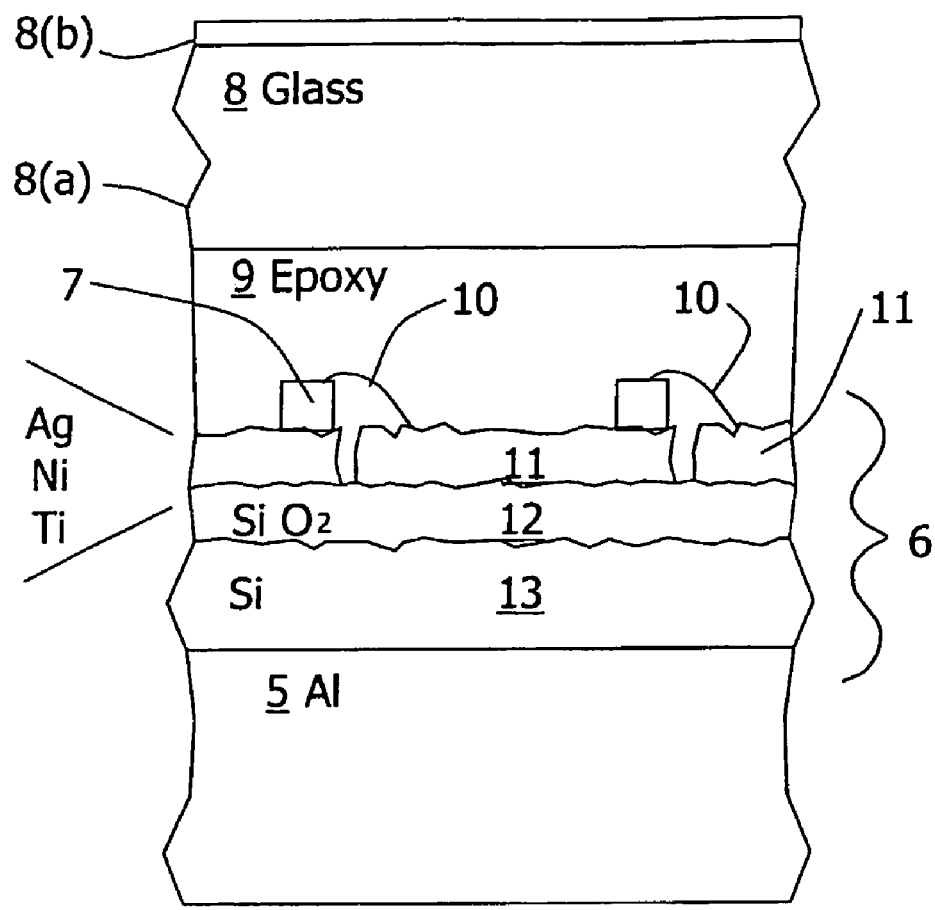
FIG. 4 is an enlarged diagrammatic cut-away cross-sectional side view showing construction of the illuminator in more detail.

Referring to FIG. 4 the structure of the illuminator 1 is shown in more detail. The substrate 6, residing on the Al casing base 5 (2 mm thick), comprises in sequence upwardly:— a silicon wafer 13 of 0.55 mm thickness, with its rough surface facing upwardly;

an $SiO_2$ oxide layer 12 of c.3 μm thickness on the Si surface, and having a rough upper surface because of roughness of the underlying Si surface;

the metal pads 11 of c.3 μm thickness and each comprising, in sequence upwardly, Ti, Ni, and Ag.

In the manufacturing process a top layer of Ti/Ni/Ag is etched following a photolithographic process to form the pattern of the pads 11 over the $SiO_2$ oxide 12. The etching pattern is that illustrated in FIG. 3.

The diodes 7 are placed on the pads 11 as shown in FIG. 3 and are encapsulated with the epoxy 9 to a depth of 1.5 mm. The opal glass diffuser plate 8 is then placed on top and is retained by the casing side walls 4. The plate 8 comprises a glass portion 8(a) on top of which there is a flash diffusion coating 8(b). The plate 8 and the epoxy 9 are carefully chosen to ensure that their refractive indexes match, in this embodiment being of a value approximately 1.47. The thickness of the plate 8 is 3.5 mm.

As illustrated in FIG. 4 the surface roughness of the Si 13 is carried through the $SiO_2$ 12 and the pads 11 so that the top surfaces of the pads 11 are rough and, being of A are also reflective.

Thus, the pads 11 act as a lower diffuser to improve optical efficiency. This is shown diagrammatically in FIG. 5(a) which illustrates operation of the illuminator before application of the diffuser plate 8. Lateral light from a diode 7 is reflected as a "beam" A at a small angle so that there is no reflection at the epoxy/air interface and it exits. Likewise for a "beam" B from another diode 7. For "beams" C and D there is internal reflection over the cross-sectional area illustrated. However because of the rough but reflective surfaces of the pads 11 a large proportion of the "beams" are reflected from one of the pads 11 at a small enough angle to exit from the epoxy 9.

Figure 5A:
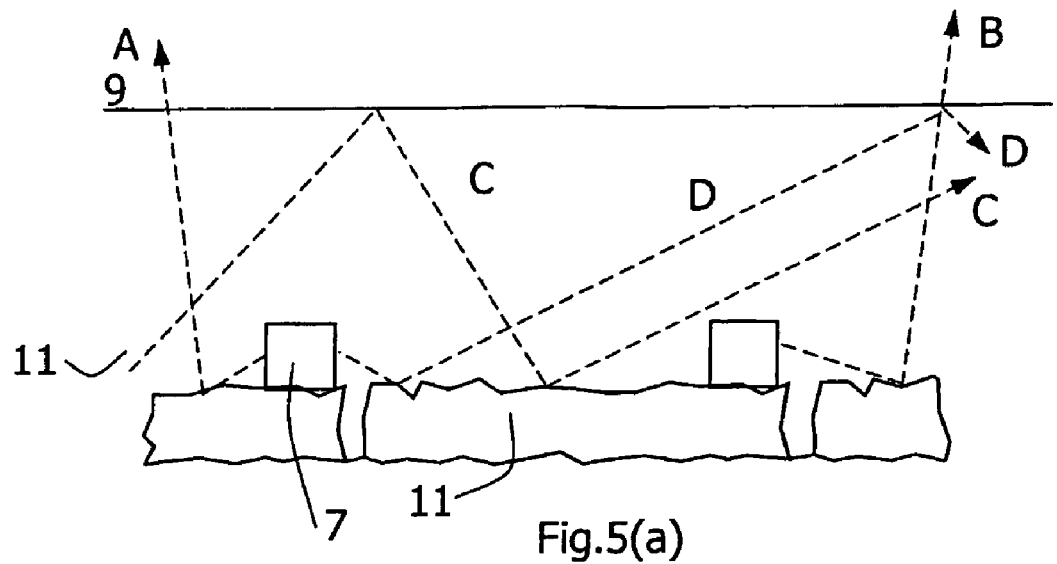
FIGS. 5(a) and 5(b) are diagrams illustrating operation of the illuminator.
Figure 5B:
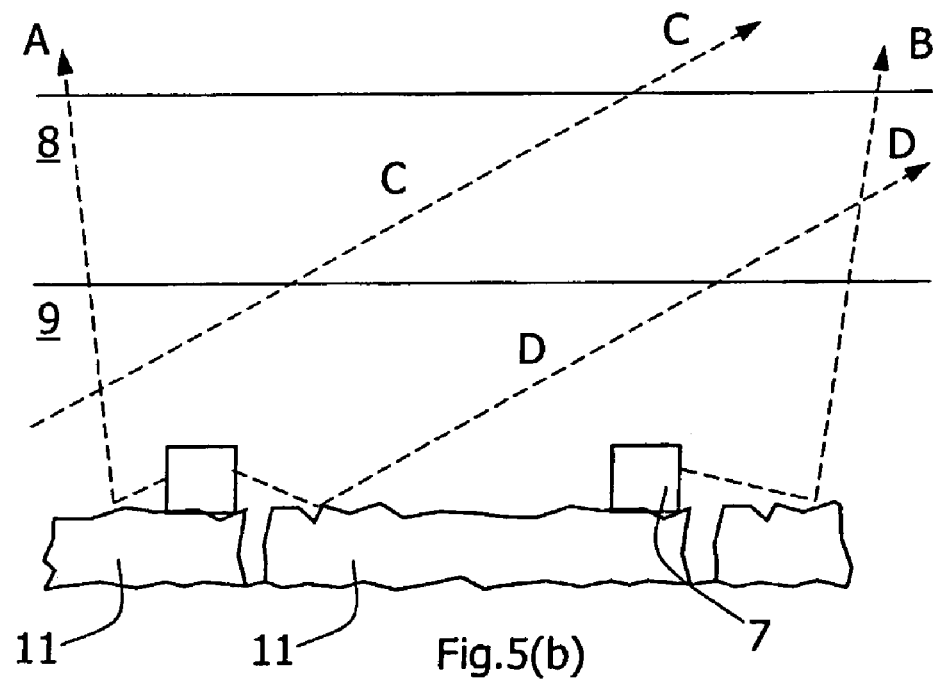

Therefore, it has been found that an illuminator as shown in FIG. 5(a) without an upper diffuser provides better optical efficiency than one having flat pad surfaces, particularly if the prior approach of a much greater diode/pad footprint ratio is used. The present invention therefore includes the embodiment of FIG. 5(a).

When the diffuser plate 8 is placed on top there is even greater optical efficiency. For example, the "beam" C which was reflected from the epoxy/air interface of FIG. 5(a) now continues through the plate 8 (index matched to 9) and exits because of the flash diffusion coating 8(b) of the plate 8.

The following are some experimental results.

|  | Bare Die on Substrate | Epoxy Covering Die | Opal Glass over epoxy & index matched |
|---|---|---|---|
| Luminous Flux (Lumens) | 4.45 | 5.5 | 6.42 |
| % increase in efficiency |  | 21.4% | 16.7% |

The illuminator of the invention could find application in a variety of fields because of its robust optical efficiency and brightness characteristics. For example, it may be used in a hazardous environment, possibly submerged in a liquid.

The invention is not limited to the embodiments described but may be varied in construction and detail. For example, the casing material may alternatively be ceramic or plastics. The choice of casing material depends to a large extent on the intended duty cycle, ceramic or metal for high duty cycle and plastics for low duty cycle. The top diffuser plate may be of the type having a roughened surface instead of a flash opal diffusion coating. Also different materials systems may be used for the substrate. While silicon is a good thermal conductor, if the duty cycle is low a material having a lower thermal conductivity may be used. Also, as described above it is not essential that the illuminator has a top diffuser. It is also envisaged that the illuminator may not have a lower diffuser on the substrate surface, only a top diffuser. In the latter embodiment, the features of use of encapsulant on the diodes index matched to a top diffuser achieves significant advantages over the prior art.

Also, the overall configuration of the illuminator may be different, such as linear or annular. The shape of the pads may be other than rectangular, such as circular or hexagonal. Also, there may be more than one diode on each pad. Also, the electrical connectivity between diodes may be different.

The invention claimed is:

1. An illuminator comprising:
   a substrate;
   an array of pre-formed LED semiconductor diodes comprising an inorganic semiconductor material placed on the substrate;
   a layer of encapsulant over the array of diodes and the substrate;
   a lower diffuser comprising a rough, reflective upper surface of the substrate that is between the placed diodes;
   an upper diffuser arranged above the layer of encapsulant, wherein the upper diffuser and the layer of encapsulant are index matched;
   wherein the substrate comprises a Si layer having a rough upper surface, an Si02 oxide on the Si layer upper surface and having a rough upper surface, and at least one metal layer over the Si02 oxide layer and having a rough upper surface; and
   wherein the substrate comprises conductive pads on which the diodes are placed.

2. The illuminator as claimed in claim 1, wherein the upper diffuser is mounted on the encapsulant.

3. The illuminator as claimed in claim 2, wherein the upper diffuser comprises an opal glass diffuser plate.

4. The illuminator of claim 1, wherein the substrate comprises conductive pads on which the diodes are placed.

5. The illuminator as claimed in claim 4, wherein the metal is Ag.

6. An illuminator as claimed in claim 5, wherein the Ag is a layer over layers of Ni and Ti.

7. The illuminator as claimed in claim 4, wherein the ratio of the footprint of the diodes to that of the pads is equal to or less than approximately 1:50.

8. The illuminator as claimed in claim 4, wherein the pads are of rectangular shape in plan.

9. The illuminator as claimed in claim 8, wherein there is a two-dimensional array of pads, and the diodes are connected in series along lines of the array between end rails.

10. The illuminator as claimed in claim 9, wherein alternate lines of diodes are located at opposed ends of their pads.

* * * * *